(12) United States Patent
Millar et al.

(10) Patent No.: US 9,772,431 B2
(45) Date of Patent: Sep. 26, 2017

(54) TERAHERTZ FREQUENCY TAGS AND METHODS FOR THEIR PREPARATION AND USE

(71) Applicant: EMPIRE TECHNOLOGY DEVELOPMENT LLC, Wilmington, DE (US)

(72) Inventors: Benjamin William Millar, Rosebery (AU); Michael Keoni Manion, Cronulla (AU); George Charles Peppou, Hornsby Heights (AU)

(73) Assignee: Empire Technology Development LLC, Wilmington, DE (US)

( * ) Notice: Subject to any disclaimer, the term of this patent is extended or adjusted under 35 U.S.C. 154(b) by 0 days.

(21) Appl. No.: 14/889,780

(22) PCT Filed: May 7, 2013

(86) PCT No.: PCT/US2013/039849
§ 371 (c)(1),
(2) Date: Nov. 6, 2015

(87) PCT Pub. No.: WO2014/182283
PCT Pub. Date: Nov. 13, 2014

(65) Prior Publication Data
US 2016/0103256 A1    Apr. 14, 2016

(51) Int. Cl.
*G06K 7/10*        (2006.01)
*G02B 5/124*       (2006.01)
(Continued)

(52) U.S. Cl.
CPC ........... *G02B 5/124* (2013.01); *G02B 5/0858* (2013.01); *G06K 19/0614* (2013.01);
(Continued)

(58) Field of Classification Search
USPC ........ 235/375, 383, 451, 457, 468, 492, 491
See application file for complete search history.

(56) References Cited

U.S. PATENT DOCUMENTS

| 4,155,793 A | 5/1979 | Salemme et al. |
| 6,246,062 B1 * | 6/2001 | Ross, III ............... B65B 25/008 250/461.1 |

(Continued)

FOREIGN PATENT DOCUMENTS

| JP | 2007010893 A | 1/2007 |
| JP | 2007101947 A | 4/2007 |

OTHER PUBLICATIONS

"Dendrimer," accessed at http://web.archive.org/web/20120116202616/http://en.wikipedia.org/wiki/Dendrimer, last modified on Nov. 28, 2011, pp. 7.

(Continued)

*Primary Examiner* — Tuyen K Vo
(74) *Attorney, Agent, or Firm* — Pepper Hamilton LLP

(57) ABSTRACT

Embodiments described herein provide for terahertz tags and methods of making and using them. A tag may include a terahertz reflective material; and a saturated hygroscopic material positioned on the terahertz reflective material. A tag may include a terahertz reflective material; and an anhydrous hygroscopic material positioned on the terahertz reflective material. A humidity sensor may include a terahertz reflective material; and an anhydrous hygroscopic material positioned on the terahertz reflective material. A temperature sensor may include a terahertz reflective material; an anhydrous hygroscopic material positioned on the terahertz reflective material; and a polymer overlay having thermally controlled water permeability disposed on the anhydrous hygroscopic material. Some embodiments relate to a tag identification device configured to transmit an (Continued)

incident signal toward the tag, and to receive a reply signal from the tag in response to the incident signal.

25 Claims, 7 Drawing Sheets

(51) Int. Cl.
```
G02B 5/08       (2006.01)
G06K 19/06      (2006.01)
G06K 19/077     (2006.01)
G06Q 10/08      (2012.01)
G01N 21/3581    (2014.01)
```
(52) U.S. Cl.
CPC ..... *G06K 19/06159* (2013.01); *G06K 19/077* (2013.01); *G06Q 10/087* (2013.01); *G01N 21/3581* (2013.01)

(56) References Cited

U.S. PATENT DOCUMENTS

| | | | |
|---|---|---|---|
| 6,656,319 B1 | 12/2003 | Boyd et al. | |
| 6,818,276 B2* | 11/2004 | Bourdelais | B32B 7/02 359/642 |
| 7,288,320 B2 | 10/2007 | Steenblik et al. | |
| 7,710,629 B2 | 5/2010 | Palmateer | |
| 7,917,298 B1 | 3/2011 | Scher et al. | |
| 8,113,427 B2 | 2/2012 | Ross et al. | |
| 2002/0068018 A1 | 6/2002 | Pepper et al. | |
| 2004/0026684 A1 | 2/2004 | Empedocles | |
| 2004/0066273 A1 | 4/2004 | Cortina et al. | |
| 2006/0080819 A1* | 4/2006 | McAllister | G06K 17/00 29/403.3 |
| 2006/0202032 A1* | 9/2006 | Kricorissian | G06K 7/0004 235/435 |
| 2006/0231625 A1 | 10/2006 | Cumming et al. | |
| 2007/0008112 A1* | 1/2007 | Covannon | A61J 3/007 340/539.12 |
| 2007/0096916 A1* | 5/2007 | Liu | G06K 7/10178 340/572.7 |
| 2007/0212266 A1 | 9/2007 | Johnston et al. | |
| 2007/0281657 A1 | 12/2007 | Brommer et al. | |
| 2007/0285843 A1 | 12/2007 | Tran | |
| 2008/0024872 A1 | 1/2008 | Dunn et al. | |
| 2008/0150688 A1 | 6/2008 | Burr | |
| 2008/0238627 A1 | 10/2008 | Oldham et al. | |
| 2009/0026016 A1* | 1/2009 | Matumura | B23Q 17/00 184/6.14 |
| 2009/0039158 A1 | 2/2009 | Grishin et al. | |
| 2010/0096181 A1* | 4/2010 | Nakamura | B32B 7/02 174/394 |
| 2010/0148050 A1 | 6/2010 | Bari | |
| 2011/0003279 A1 | 1/2011 | Patel | |
| 2011/0017911 A1* | 1/2011 | Flamanc | C09D 7/1216 250/361 R |
| 2011/0198501 A1 | 8/2011 | Ouchi et al. | |
| 2011/0245460 A1 | 10/2011 | Livingston et al. | |
| 2011/0253744 A1 | 10/2011 | Pelfrey | |
| 2012/0045787 A1* | 2/2012 | Boettiger | G01N 21/03 435/29 |
| 2012/0055013 A1 | 3/2012 | Finn | |
| 2012/0251125 A1 | 10/2012 | Harman | |
| 2013/0082458 A1* | 4/2013 | O'Boyle | G03H 1/0252 283/109 |
| 2013/0278413 A1 | 10/2013 | Kamath et al. | |
| 2014/0209691 A1 | 7/2014 | Finn et al. | |

OTHER PUBLICATIONS

"Engineers demonstrate first room-temperature semiconductor source of coherent Terahertz radiation," accessed at http://web.archive.org/web/20120730085014/http://m.phys.org/_news130385859.html, pp. 2 (May 19, 2008).

"Faculteit Technische Natuurkunde Ultrabright THz source," accessed at http://web.archive.org/web/20111230114442/http://www.tue.nl/universiteit/faculteiten/faculteit-tn/onderzoek/onderzoekscluster-plasmas-en-straling/coherence-and-quantum-technology-cqt/research/laser-assisted-accelerators/ultrabright-thz-source, pp. 5 (Nov. 13, 2015).

"Thermo Scientific™ Pierce™ Protein Biology," Thermo Fisher Scientific, accessed at https://www.thermofisher.com/in/en/home/brands/thermo-scientific/pierce-protein-biology.html#/legacy=piercenet.com, accessed on, pp. 2 (Nov. 12, 2015).

"THz Materials," Tydex J.S.Co., accessed at http://web.archive.org/web/20110504082942/http://www.tydexoptics.com/pdf/THz_Materials.pdf, pp. 1-5 (May 4, 2011).

"What is Terahertz?," Teraview , accessed at http://web.archive.org/web/20120820234809/http://www.teraview.com/about/what-is-terahertz-thz.html, pp. 2 (Nov. 13, 2015).

Berland, Photovoltaic Technologies Beyond the Horizon: Optical Rectenna Solar Cell, Final Report, National Renewable Energy Laboratory, pp. 1-21 (Aug. 1, 2001-Sep. 30, 2002).

Bernier et al., Terahertz encoding approach for secured chipless radio frequency identification, Journal of Applied Optics, 50(23) pp. 4648-4655 (Aug. 10, 2011).

Bharadwaj et al., Optical Antennas, Advances in Optics and Photonics, 1(3) pp. 438-483 (Aug. 11, 2009).

Biagioni et al., Nanoantennas for visible and infrared radiation, Rep. Prog. Phys., 75(2) pp. 024402-024442 (2012).

Boyle, Terahertz-Band Mobile Phones Could See Through Walls, accessed at http://web.archive.org/web/20120626110318/http://www.popsci.com.au/technology/terahertz-band-mobile-phones-could-see-through-walls, pp. 3 (Apr. 19, 2012).

Choi et al., Fabrication of Conducting Polymer Nanowires, Nanowires—Implementations and Applications, Chapter 19, pp. 440-454 (Jul. 18, 2011).

Cooper et al., THz Imaging Radar for Standoff Personnel Screening, IEEE Transactions on Terahertz Science and Technology, 1(1) pp. 169-182 (Sep. 2011).

Courtland, A Cheap Terahertz Camera, accessed at http://web.archive.org/web/20120606044708/http://spectrum.ieee.org/semiconductors/optoelectronics/a-cheap-terahertz-camera, pp. 2 (Apr. 2012).

Dryness, Everything You Wanted to Know About Silica Gel but Didn't Know Who to Ask, Yahoo, accessed at https://web.archive.org/web/20130117065501/http://voices.yahoo.com/everything-wanted-know-silica-gel-but-3343922.html?, pp. 4 (May 21, 2009).

Grossman et al., Terahertz Imaging and Security Applications, National Institute of Standards & Technology, Quantum Electrical Metrology Division, pp. 1-57 (Nov. 17, 2004).

Hamilton, Water Vapor Permeability of Polyethylene and Other Plastic Materials, The Bell System Technical Journal, 46(2) pp. 391-415 (Feb. 1967).

Hirsch et al., Nanoshell-mediated near-infrared thermal therapy of tumors under magnetic resonance guidance, PNAS, 100(23) pp. 13549-13554 (Nov. 11, 2003).

Humpries, Future smartphone cameras to see through walls, accessed at http://web.archive.org/web/20120422045815/http://www.geek.com/articles/mobile/future-smartphone-cameras-to-see-through-walls-20120419, pp. 5 (Apr. 19, 2012).

International Search Report and Written Opinion for International Application No. PCT/US2012/050744, mailed on Oct. 23, 2012.

International Search Report and Written Opinion for International Application No. PCT/US2013/039849, mailed on Oct. 23, 2012.

Jeon et al., Electrical characterization of conducting polypyrrole by THz time-domain spectroscopy, Appl. Phys. Lett., 77(16) pp. 2452-2454 (Oct. 16, 2000).

Lin et al., Smart temperature-controlled water vapor permeable polyurethane film, Journal of Membrane Science, 299 (1-2) pp. 91-96 (Aug. 2007).

Mayes, Miniature field deployable Terahertz source, Proceedings of the SPIE, (6212) pp. 1-11 (May 19, 2006).

Ohgai, Fabrication of Functional Metallic Nanowires Using Electrodeposition Technique, Electrodeposited Nanowires and their Applications, (3) pp. 62-84 (Feb. 1, 2010).

(56) References Cited

OTHER PUBLICATIONS

Pastore et al., Fabrication of ultra thin anodic aluminium oxide membranes by low anodization voltages, IOP Conference Series: Materials Science and Engineering, 23(1) pp. 12025-12028 (2011).
She et al., Electrodeposition of One-Dimensional Nanostructures, Recent Patents on Nanotechnology, (3) pp. 182-191 (2009).
Shenoy et al., Surface functionalization of gold nanoparticles using hetero-bifunctional poly (ethylene glycol) spacer for intracellular tracking and delivery, International Journal of Nanomedicine, 1(1) pp. 51-57 (Mar. 2006).
Wang et al., The physical theory and propagation model of THz atmospheric propagation, Journal of Physics: Conference Series, (276) pp. 12223-12233 (2011).
Williams et al., Optically Coded Nanocrystal Taggants and Optical Frequency IDs, Proc. SPIE 7673, Advanced Environmental, Chemical, and Biological Sensing Technologies VII, 76730M, pp. 1-14 (Apr. 24, 2010).

\* cited by examiner

TERAHERTZ FREQUENCY TAGS AND METHODS FOR THEIR PREPARATION AND USE

CROSS REFERENCE TO RELATED APPLICATION

This application is a U.S. National Stage filing under 35 U.S.C. §371 of International Application Ser. No. PCT/US2013/039849 filed on May 7, 2013 entitled "TERAHERTZ FREQUENCY TAGS AND METHODS FOR THEIR PREPARATION AND USE," which is incorporated herein by reference in its entirety.

BACKGROUND

The ability to identify individual tagged items contained within external packaging obscured from visual inspection may improve efficiency and management of stock. Furthermore, the ability to determine an item's environmental conditions within large bulk packaging rapidly and non-invasively can improve stock management, mitigation of product damage and maintenance of sterile environments.

Existing penetrating radiation identification and security tags (including terahertz (THz) and microwave) suffer from serious impediments to usability and thus their ability to address the above issues. These impediments may arise due to the use of partial transmission or dependence on focused beams. For example, retrieving data from a tag by transmitting radiation through the tag requires a large receiver to detect the transmitted radiation. Such a receiver adds cost and complexity to a system and renders the tag unusable if it is positioned in close proximity to a non-transmissive object (e.g. any metal or moisture-containing material within the packaging). For similar reasons, the use of a reflective surface or a perforation contrast for tags may not provide sufficient contrast for reading the tag. This limits the distance from which the tag may be read and precludes it from use on a wide range of products for which it may otherwise be useful, such as appliances and foodstuffs.

Additionally, focused and highly coherent beams or penetrating laser beams, required for reading some existing tags, are expensive to produce, require bulky equipment with extensive cooling systems to operate, and provide only a narrow readable angle. Such reader-tag systems require accurate targeting of the tag, and thus are only usable at close range, as the resolution rapidly degrades over distance. Accordingly, there is a need for a tag that is readable, preferably from a single handheld instrument, via high contrast reflection over a wide detection angle.

SUMMARY

Embodiments described in this document relate to terahertz tags and methods of making and using them. In some embodiments, a tag may include a terahertz reflective material; and a saturated hygroscopic material positioned on the terahertz reflective material. In some embodiments, a method of making a tag may include providing a terahertz reflective material; providing a saturated hygroscopic material; and positioning the saturated hygroscopic material on the terahertz reflective material.

In some embodiments, a tag identification system may include a tag having a saturated hygroscopic material positioned on a terahertz reflective material; and a tag identification device configured to transmit an incident signal toward the tag, and to receive a reply signal from the tag in response to the incident signal. In some embodiments, a method of using a tag identification system may include transmitting an incident signal toward a tag including a saturated hygroscopic material deposited on a terahertz reflective material, and receiving a reply signal from the tag in response to the incident signal.

In some embodiments, a humidity sensor may include a terahertz reflective material; and an anhydrous hygroscopic material positioned on the terahertz reflective material. In some embodiments, a method of making a humidity sensor may include providing a terahertz reflective material; providing an anhydrous hygroscopic material; and positioning the anhydrous hygroscopic material on the terahertz reflective material.

In some embodiments, a humidity identification system may include a humidity sensor having an anhydrous hygroscopic material positioned on a terahertz reflective material, where at least a portion of the anhydrous hygroscopic material is configured to be hydrated when the humidity sensor is exposed to humidity to form a saturated hygroscopic material, and a humidity sensor identification device configured to transmit an incident signal toward the humidity sensor and to receive a reply signal from the humidity sensor in response to the incident signal. In some embodiments, a method of using a humidity identification system may include transmitting an incident signal toward a humidity sensor having an anhydrous hygroscopic material positioned on a terahertz reflective material, where at least a portion of the anhydrous hygroscopic material is configured to be hydrated when the humidity sensor is exposed to humidity to form a saturated hygroscopic material, and receiving a reply signal from the humidity sensor in response to the incident signal.

In some embodiments, a temperature sensor may include a terahertz reflective material; an anhydrous hygroscopic material positioned on the terahertz reflective material; and a polymer overlay having thermally controlled water permeability disposed on the anhydrous hygroscopic material to seal the hygroscopic material on the terahertz reflective material. In some embodiments, a method of making a temperature sensor may include providing a terahertz reflective material; providing an anhydrous hygroscopic material; positioning the anhydrous hygroscopic material on the terahertz reflective material; and sealing the anhydrous hygroscopic material on the terahertz reflective material with a polymer overlay having thermally controlled water permeability.

In some embodiments, a temperature identification system may include a temperature sensor having an anhydrous hygroscopic material deposited on a terahertz reflective material and a polymer overlay having thermally controlled water permeability disposed on the anhydrous hygroscopic material to seal the anhydrous hygroscopic material on the terahertz reflective material, where at least a portion of the anhydrous hygroscopic material is configured to be hydrated when the temperature sensor is exposed to a temperature to form a saturated hygroscopic material, and a temperature sensor identification device configured to transmit an incident signal toward the temperature sensor, and to receive a reply signal from the temperature sensor in response to the incident signal.

In some embodiments, a method of using a temperature identification system may include transmitting an incident signal toward a temperature sensor including an anhydrous hygroscopic material positioned on a terahertz reflective material and a polymer overlay having thermally controlled water permeability positioned on the anhydrous hygroscopic material to seal the anhydrous hygroscopic material on the terahertz reflective material, where at least a portion of the anhydrous hygroscopic material is configured to be hydrated when the temperature sensor is exposed to a temperature to form a saturated hygroscopic material, and receiving a reply signal from the temperature sensor in response to the incident signal.

In some embodiments, a tag may include a terahertz reflective material; an anhydrous hygroscopic material positioned on the terahertz reflective material; and a polymer overlay positioned on the anhydrous hygroscopic material to seal the anhydrous hygroscopic material on the terahertz reflective material.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

Figure 1:
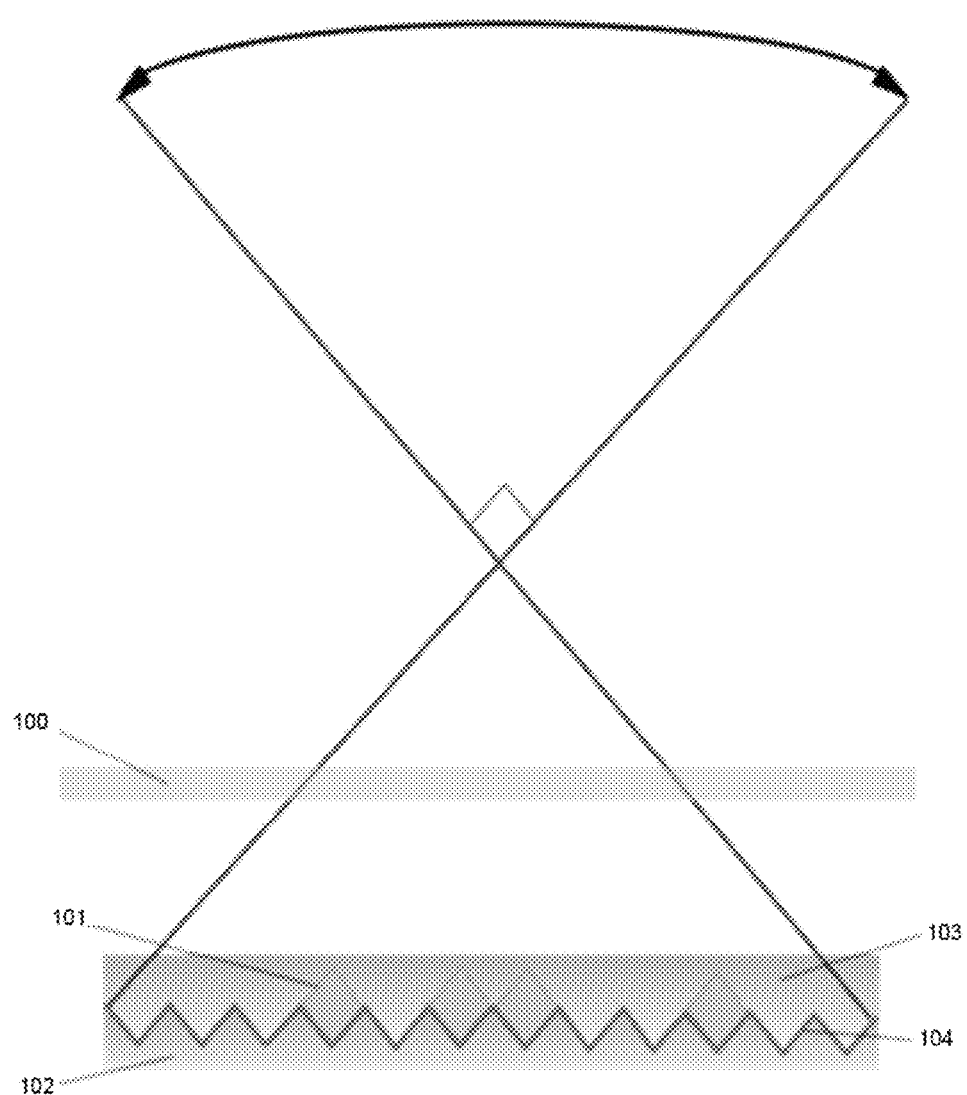
FIG. 1 depicts a cross-sectional view of an illustrative tag according to an embodiment described herein.

In the following detailed description, reference is made to the accompanying drawings, which form a part of this document. In the drawings, similar symbols typically identify similar components, unless the context dictates otherwise. The illustrative embodiments described in the detailed description, drawings, and claims are not meant to be limiting. Other embodiments may be used, and other changes may be made, without departing from the spirit or scope of the subject matter presented in this document. It will be readily understood that the aspects of the present disclosure, as generally described in this document, and illustrated in the Figures, can be arranged, substituted, combined, separated, and designed in a wide variety of different configurations, all of which are explicitly contemplated to be within the scope of this disclosure.

Figure 7:
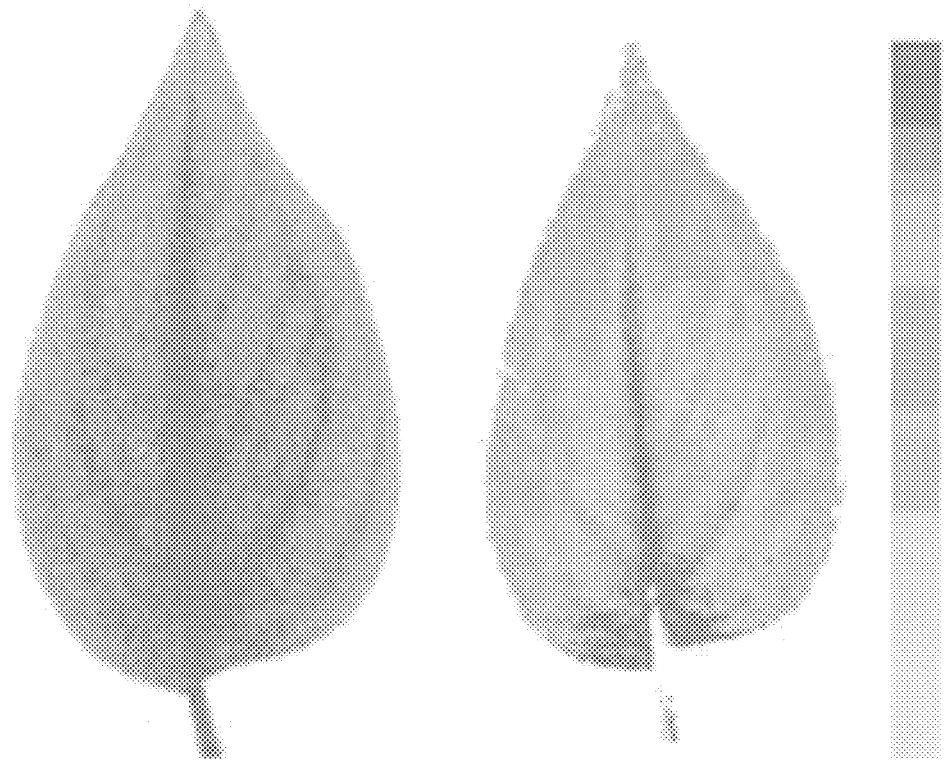
FIG. 7 illustrates images obtained by terahertz imaging of a leaf before and after moisture evaporation.

The terahertz (THz) frequency band of the electromagnetic spectrum penetrates many different 'soft' materials (for example, cardboard, plastic, ceramic, fabric, and the like), with the key exceptions of reflective metals and absorbent molecules, such as water. The terahertz band of the electromagnetic spectrum includes frequencies between the high-frequency edge of the microwave band (about 300 GHz) and the long-wavelength edge of far-infrared light (about 3 THz), which corresponds to waves having a wavelength of about 0.03 mm to about 1.0 mm. By measuring the absorbance of terahertz rays, it is possible to show a detailed imaging of moisture in a leaf. For example, FIG. 7 illustrates that a relatively high level of detail of moisture distribution in a leaf can be achieved using T-ray imaging. On the far left of FIG. 7 is a terahertz image of a leaf. The leaf includes regions of darker and lighter shades of grey, with the darker shades showing a higher moisture content and the lighter shades showing a lower moisture content. In the middle of FIG. 7 is a terahertz image of the same leaf after 48 hours, showing a non-uniform evaporation of water from the leaf as can be seen from the non-uniform distribution of the dark grey regions. On the far right is a color bar indicating the relative concentration of water within the leaf. The relative concentration increases from the bottom of the bar where the color is a light grey, to the top where the color is a darkest shade of grey.

Embodiments described in this document provide for a tag that can be read through optically opaque obstructions using the terahertz frequency band of the electromagnetic spectrum. In some embodiments, the tag is encoded by a terahertz reflective material, such as, for example, thin film metallic coatings, and an absorbent coordinated hygroscopic material, which when hydrated is terahertz opaque. At least one of the advantages of the tags of embodiments herein is that the contrast between reflectance and absorbance patterns of metallic surfaces and water molecules allows the tag to be clearly readable regardless of surroundings or packaging. Another exemplary advantage of the disclosed tags is the ability to manufacture such tags using inexpensive, readily available materials.

In some embodiments, a tag may include an encoded one-dimensional label, two-dimensional label, or multi-dimensional label. In some embodiments, a tag may include a simple intrinsic sensor system designed to detect certain environmental changes.

As used herein, the term "reflective well" or a "retro-reflective well" refers to a well, pit, hollow, dip, dimple, indent, dent, depression or the like that is capable of reflecting electromagnetic waves. In some embodiments, the reflective well or "retro-reflective well" is capable of reflecting terahertz waves. In some embodiments, a reflective well may have a width equal to or greater than about 0.1 mm, or equal to or greater than about 0.2 mm. In some embodiments, a reflective well may have a width equal to or less than about 100 mm, equal to or less than about 150 mm, or equal to or less than about 200 mm. In some embodiments, a reflective well may have a width of about 0.1 mm to about 200 mm, about 0.1 mm to about 150 mm, about 0.1 mm to about 100 mm, 0.2 mm to about 200 mm, about 0.2 mm to about 150 mm, about 0.2 mm to about 100 mm, about 0.2 mm to about 50 mm, about 1 mm to about 200 mm, about 1 mm to about 150 mm, about 1 mm to about 100 mm, or about 1 mm to about 50 mm. In some embodiments, a reflective well may have a width of about 0.1 mm, about 0.2 mm, about 0.5 mm, about 1 mm, about 5 mm, about 10 mm, about 20 mm, about 30 mm, about 40 mm, about 50 mm, about 60 mm, about 70 mm, about 80 mm, about 90 mm, about 100 mm, about 120 mm, about 140 mm, about 160 mm, about 180 mm, about 200 mm, or a range between any two of these values.

As used herein, the term "electromagnetic waves" refers to radiation that is used to interrogate a tag, is incident upon a tag or reflects from a tag. In some embodiments, electromagnetic waves may be at frequencies of about 0.1 terahertz to about 10 terahertz, about 0.1 terahertz to about 5 terahertz, about 0.1 terahertz to about 3 terahertz, about 0.2 terahertz to about 10 terahertz, about 0.2 terahertz to about 5 terahertz, about 0.2 terahertz to about 3 terahertz, about 0.3 terahertz to about 10 terahertz, about 0.3 terahertz to about 5 terahertz, or about 0.3 terahertz to about 3 terahertz. In some embodiments, electromagnetic waves may be at frequencies of about 0.1 terahertz, about 0.2 terahertz, about 0.3 terahertz, about 0.5 terahertz, about 1 terahertz, about 1.5 terahertz, about 2 terahertz, about 2.5 terahertz, about 3 terahertz, about 3.5 terahertz, about 5 terahertz, about 7 terahertz, about 10 terahertz, or a range between any two of these values. In some embodiments, the electromagnetic waves may have a wavelength of about 0.03 mm to about 3.0 mm, about 0.03 mm to about 2.0 mm, about 0.03 mm to about 1.0 mm, about 0.5 mm to about 3.0 mm, about 0.5 mm to about 2.0 mm, about 0.5 mm to about 1.0 mm, or about 1 mm to about 3 mm. In some embodiments, the electromagnetic waves may have a wavelength of about 1 mm to about 2 mm, about 0.03 mm, about 0.1 mm, about 0.2 mm, about 0.3 mm, about 0.4 mm, about 0.5 mm, about 1.0 mm, about 1.5 mm, about 2.0 mm, about 2.5 mm, about 3.0 mm, or a range between any two of these values.

As used herein, a "polymer overlay" refers to a polymer disposed on the terahertz reflective material to position the hygroscopic material onto the terahertz reflective material. In some embodiments, the polymer overlay may permit certain wavelengths to pass through. In some embodiments, the polymer overlay is transmissive to electromagnetic waves having the frequencies and/or wavelengths identified above. In some embodiments, the polymer overlay is water impermeable. In some embodiments, the water-impermeable polymer overlay may include polyethylene terephthalate, polyethylene, high-density polyethylene, acrylic polymer, or a combination thereof. In some embodiments, the polymer overlay is water permeable. In some embodiments, the water permeable polymer overlay includes polyethylene oxide, microporous polyethylene, a polyethylene oxide/polybutylene terephthalate (PEO-PBT) copolymer, sulfonated polyetheretherketone (SPEEK), polydimethylsiloxane, ethyl cellulose, a woven polymer overlay of any of the foregoing, a perforated polymer overlay of any of the foregoing, or a combination thereof.

In some embodiments, the polymer overlay is water permeable at a certain temperature. In some embodiments, the polymer overlay that is water permeable at a certain temperature includes a polyurethane copolymer, an acrylic side-chain crystallizable polymer, siloxane side-chain crystallizable polymer, or a combination thereof. In some embodiments, the polymer overlay may have a critical glass transition temperature of about 0° C. to about 50° C. In some embodiments, the polymer overlay has a critical glass transition temperature of about 0° C. to about 70° C., about 0° C. to about 60° C., about 0° C. to about 40° C., about 0° C. to about 30° C., about 0° C. to about 20° C., about 5° C. to about 70° C., about 5° C. to about 60° C., about 5° C. to about 50° C., about 5° C. to about 40° C., about 5° C. to about 30° C., about 5° C. to about 20° C., about 10° C. to about 70° C., about 10° C. to about 60° C., about 10° C. to about 50° C., about 10° C. to about 40° C., about 10° C. to about 30° C., about 10° C. to about 20° C., about 20° C. to about 70° C., about 20° C. to about 60° C., about 20° C. to about 50° C., about 20° C. to about 40° C., or about 20° C. to about 30° C. In some embodiments, the polymer overlay has a critical glass transition temperature of about 5° C., about 10° C., about 15° C., about 20° C., about 25° C., about 30° C., about 35° C., about 40° C., about 45° C., about 50° C., about 60° C., about 70° C., or a range between any two of these values. The polymer overlay may be configured to be water permeable at its glass transition temperatures.

In some embodiments, the tag may further include a polymer substrate on which the terahertz reflective material is disposed. In embodiments herein, the polymer substrate may include polycarbonate, polypropylene, polyethylene, polystyrene, polyester, polyamide, acrylic, acrylonitrile-butadiene-styrene copolymer, chlorinated polyvinylchloride, natural rubber, neoprene, nitrile rubber, polyurethane, polyvinylchloride, silicone, thermoplastic elastomer, vinylidene fluoride-hexafluoropropylene copolymer, or a combination thereof. In some embodiments, the polyester may be polyethylene terephthalate.

In some embodiments, the terahertz reflective material may include at least one metallic film. In embodiments herein, the metallic film may include aluminum, gold, silver, copper, tin, silicon, zinc, nickel, chromium, an alloy of any of the foregoing, or a combination thereof.

As shown in FIG. 1, an illustrative tag may include a terahertz reflective material 104 and a saturated hygroscopic material 101 positioned on the terahertz reflective material 104. A polymer overlay 103 is provided on the saturated hygroscopic material 101 to seal the saturated hygroscopic material 101 on the terahertz reflective material 104. The tag can be interrogated by projecting terahertz radiation onto the tag, and receiving coherently reflected light from the surface of the tag. The wide 3-dimensional interrogation angle shown in FIG. 1 (by the dual arrowed line) may aid in location and targeting of the tag which cannot be seen visually, as well as improving operation with a divergent THz source. In some embodiments, the saturated hygroscopic material 101 is strongly hygroscopic.

Figure 2:
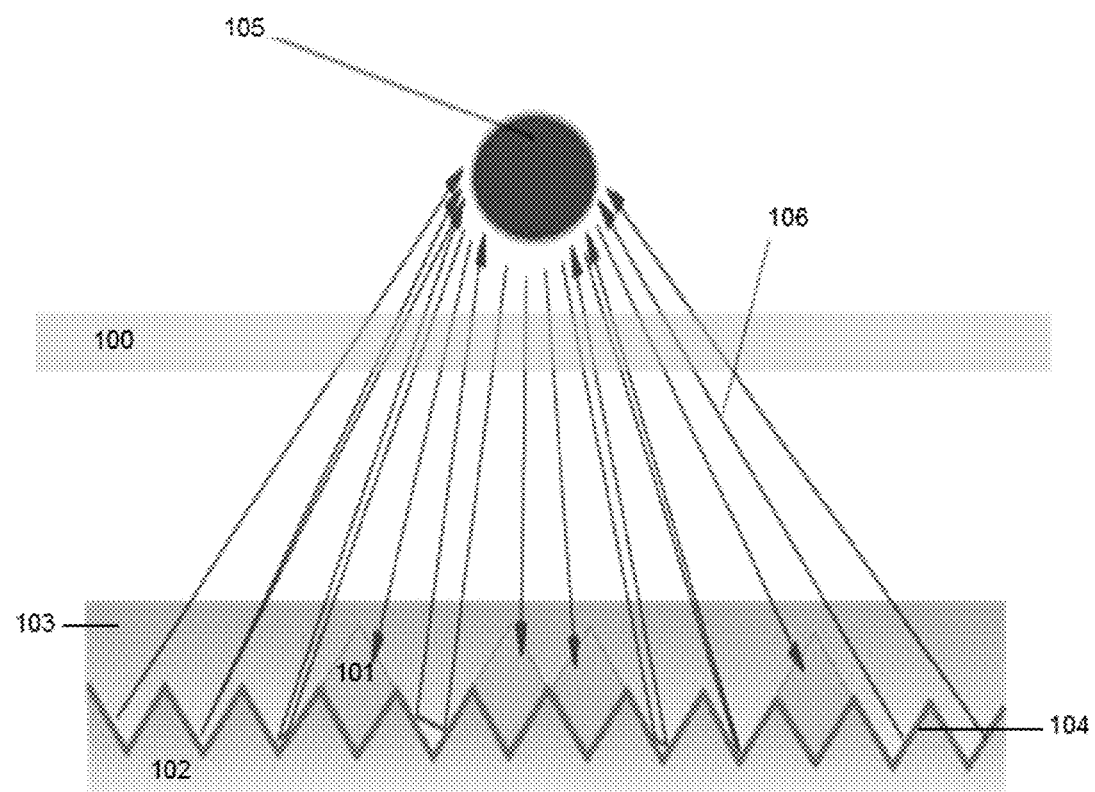
FIG. 2 depicts an illustrative method of interrogating a tag with a divergent Terahertz source according to an embodiment described herein.
Figure 3:
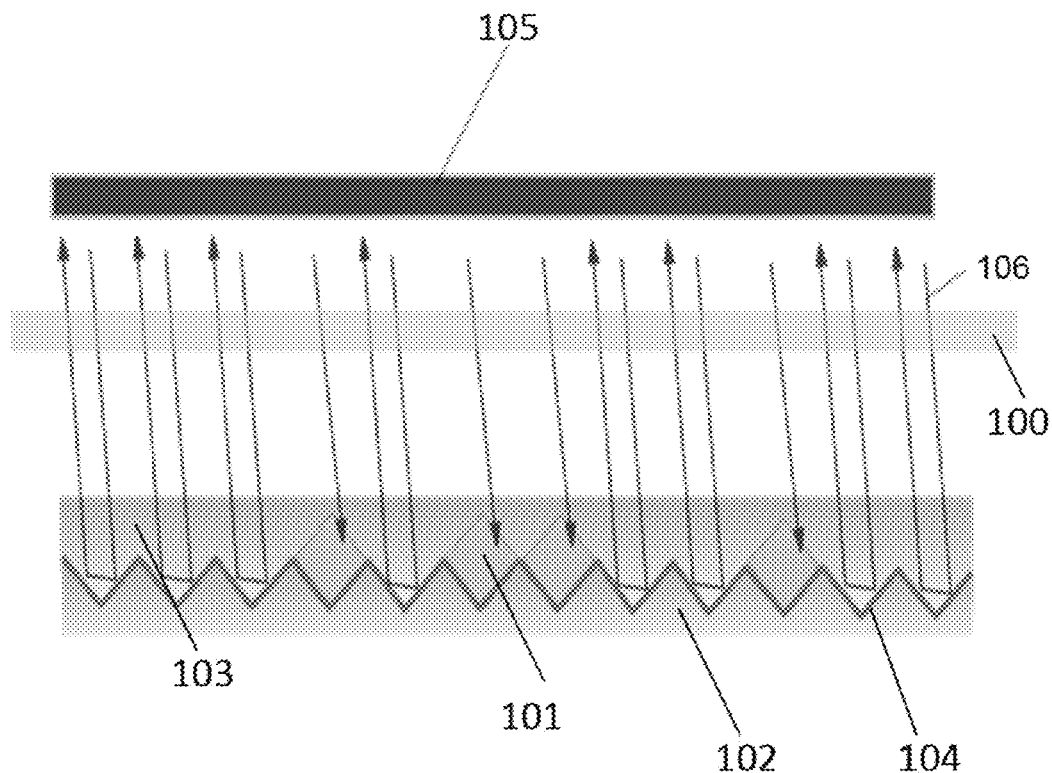
FIG. 3 depicts an illustrative method of interrogating a tag with a scanning laser system according to an embodiment described herein.

As shown in FIGS. 2 and 3, terahertz radiation may be projected by using a terahertz radiation source 105. As shown in FIG. 2, in some embodiments, the terahertz radiation source 105 can be a divergent beam that may be used to project terahertz radiation. As shown in FIG. 3, in some embodiments, terahertz radiation source 105 can be a scanning laser system that may be used to project terahertz radiation. In some embodiments, a portable terahertz source may be used to project terahertz radiation. In some embodiments, a terahertz sensitive camera may be used to receive coherently reflected light. In some embodiments, the terahertz reflective material 104 may be sheer or retro-reflexive. In some embodiments, terahertz laser reading may be performed using a sheer terahertz reflective material 104. In some embodiments, a divergent terahertz source may interrogate a retro-reflective terahertz reflective material. In some embodiments, the terahertz radiation penetrates a terahertz penetrable material 100 of packaging containing the tag. In some embodiments, the tag may be packaged in a terahertz penetrable material 100.

Some embodiments are directed to a tag including a terahertz reflective material; and a saturated hygroscopic material positioned on the terahertz reflective material. In some embodiments, the saturated hygroscopic material may include hydrous calcium chloride, hydrous calcium sulfate, hydrous potassium carbonate, hydrous sodium sulfate, hydrous cobalt (II) chloride, hydrous lithium chloride, hydrous zinc chloride, hydrous magnesium sulfate, hydrous copper sulfate, hydrous sodium tetraborate, hydrous sodium acetate, hydrous aluminum sulfate, hydrous aluminum potassium sulfate, hydrous magnesium chloride, hydrous sodium potassium tartrate, hydrous sodium thiosulfate, hydrous sodium silicate, hydrous sodium metasilicate, saturated silica gel, saturated microporous clays, saturated zeolites, saturated activated alumina, saturated activated carbon, or a combination thereof. Table 1 lists exemplary hygroscopic salts with stable hydrous and anhydrous forms that can be used as the hygroscopic material.

TABLE 1

| Anhydrous | Hydrate |
| --- | --- |
| calcium chloride ($CaCl_2$) | calcium chloride (hexahydrate) ($CaCl_2(H_2O)_6$) |
| zinc chloride ($ZnCl_2$) | zinc chloride (tetrahydrate) ($ZnCl_2(H_2O)_4$) |
| magnesium sulphate ($MgSO_4$) | magnesium sulphate (heptahydrate) ($MgSO_4 \cdot 7H_2O$) |
| copper sulphate ($CuSO_4$) | copper sulphate (pentahydrate) ($CuSO_4 \cdot 5H_2O$) |

In some embodiments, the saturated hygroscopic material is positioned on the terahertz reflective material to create a unique identifier on the tag by contrasting the reflectance of the terahertz reflective material with the absorbance of the terahertz waves in the water molecules contained in the saturated hygroscopic material. As used herein, the term saturated may refer to fully or partially hydrated hygroscopic material.

Figure 4:
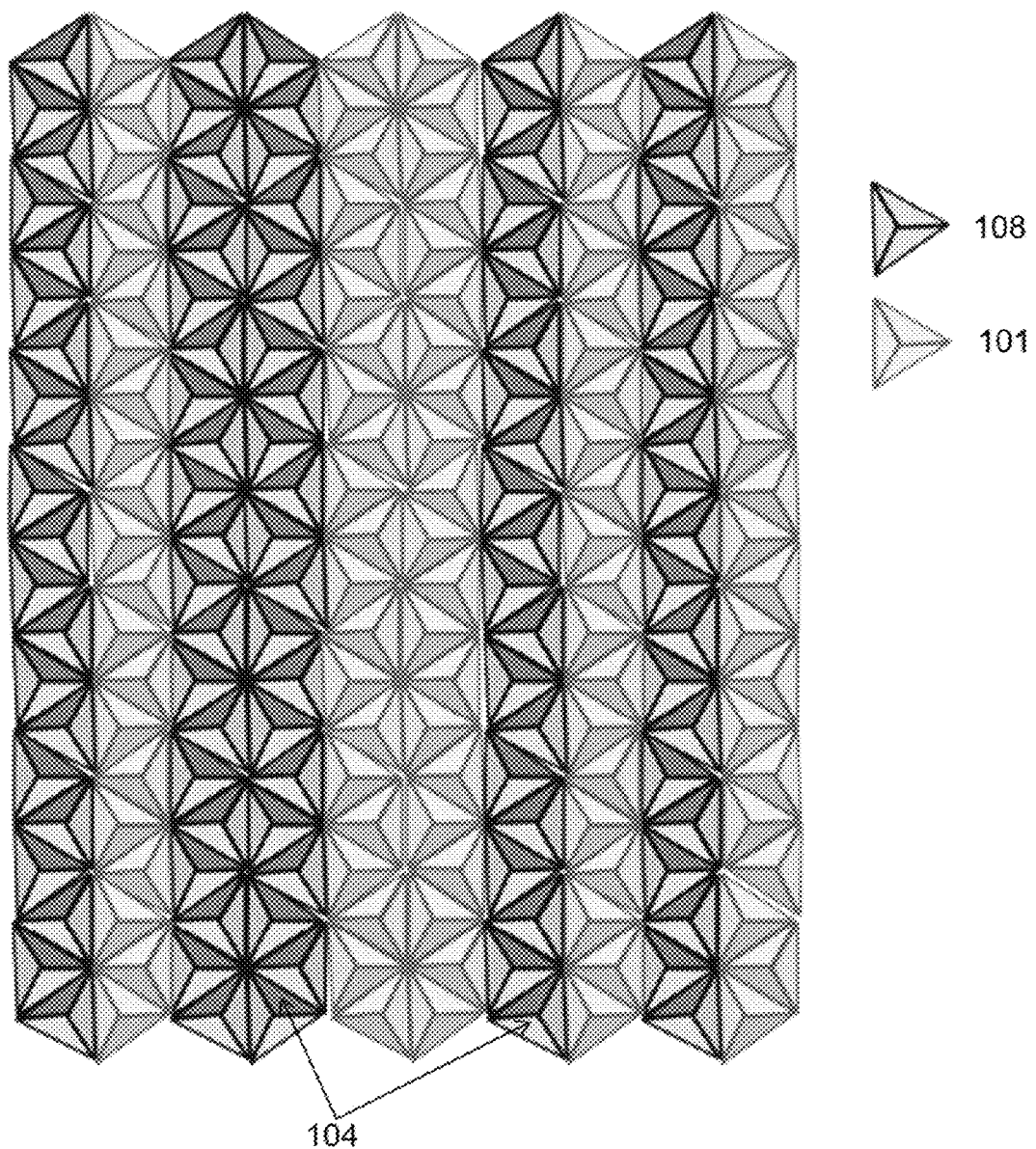
FIG. 4 depicts a top down view of an illustrative tag according to an embodiment described herein where absorbent hydrate particles (light gray) are arranged on retro-reflective aluminum wells (dark grey) to simulate a traditional barcode for reading by a scanning laser system.
Figure 5:
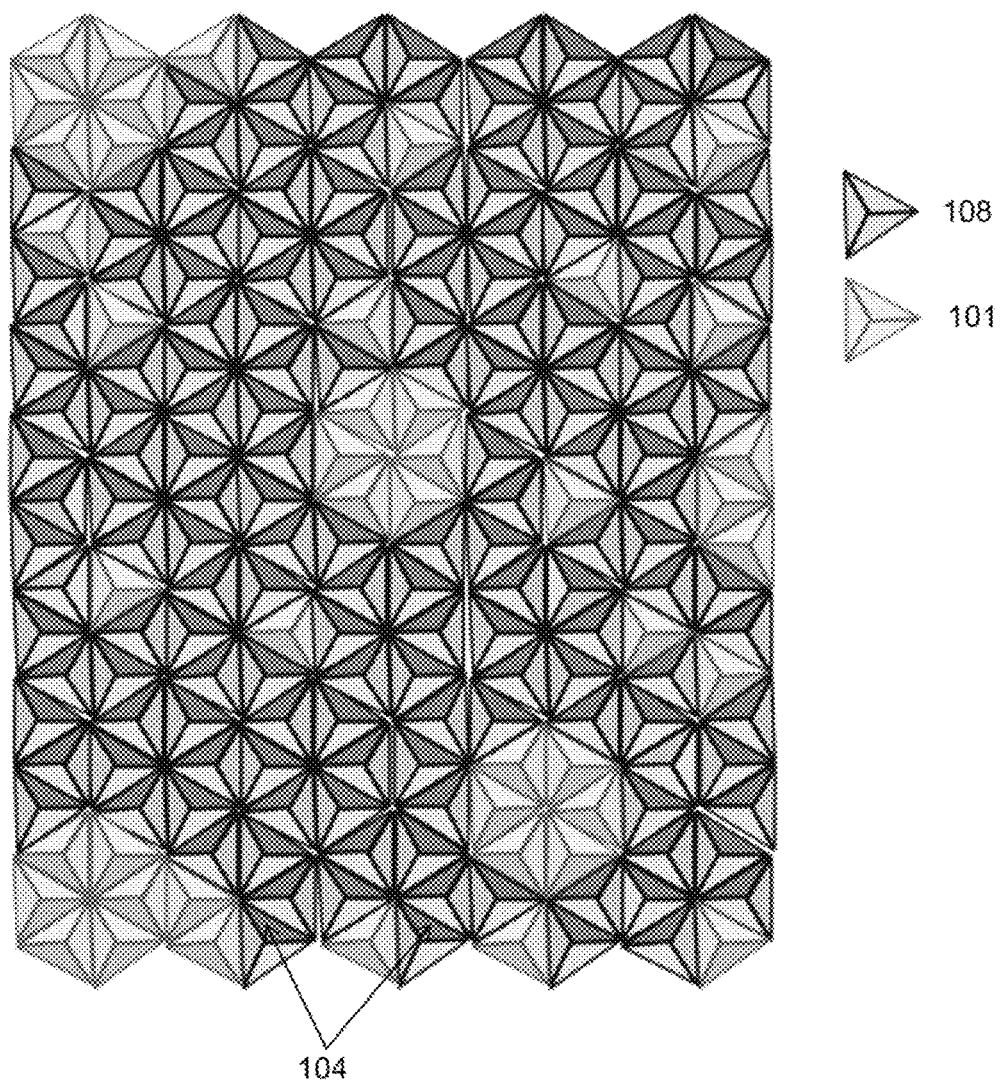
FIG. 5 depicts a top down view of an illustrative tag according to an embodiment described herein where absorbent hydrate particles (light gray) are arranged on retro-reflective aluminum wells (dark grey) to form a 2D matrix code for reading by a divergent Terahertz source.

In some embodiments, the terahertz reflective material includes a metallic film. In some embodiments, the metallic film includes the metals discussed above. In some embodiments, the terahertz reflective material is configured to be retro-reflective. As shown in FIGS. 4 and 5, in some embodiments, the terahertz reflective material 104 includes retro-reflective wells 108. In some embodiments, the terahertz reflective material is configured to be sheer. In some embodiments, the saturated hygroscopic material 101 is deposited in one or more of the retro-reflective wells 108. In some embodiments, the terahertz reflective material 104 is configured to reflect incident electromagnetic waves 106 having the frequencies and/or wavelengths identified above.

In some embodiments, the tag may further include a polymer substrate on which the terahertz reflective material is disposed. In some embodiments, the polymer substrate includes the polymers disclosed above.

In some embodiments, the saturated hygroscopic material is configured to absorb incident electromagnetic waves having the frequencies and/or wavelengths identified above.

In some embodiments, the tag may further include a polymer overlay disposed on the saturated hygroscopic material to seal the saturated hygroscopic material on the terahertz reflective material. In some embodiments, the polymer overlay is transmissive to electromagnetic waves having the frequencies and/or wavelengths identified above.

In some embodiments, a reflectance pattern is formed from absorption of incident electromagnetic waves by the saturated hygroscopic material and reflection of the incident electromagnetic waves by the terahertz reflective material. In some embodiments, the reflectance pattern is translatable into readable data. FIG. 4 illustrates a tag encoded with saturated hygroscopic material 101 that is positioned to form a reflectance pattern like a traditional barcode. In some embodiments, the barcode reflectance pattern may be read by a scanning laser reader as exemplified in FIG. 3. FIG. 5 illustrates a tag encoded with saturated hygroscopic material 101 that is positioned to form a 2D matrix reflectance pattern. In some embodiments, a 2D matrix reflectance pattern is read by a camera style divergent beam interrogator.

Some embodiments are directed to a tag identification system including a tag having a saturated hygroscopic material positioned on a terahertz reflective material; and a tag identification device configured to transmit an incident signal toward the tag, and to receive a reply signal from the tag in response to the incident signal. In some embodiments, the incident signal includes electromagnetic waves having the frequencies and/or wavelengths identified above. In some embodiments, the reply signal includes electromagnetic waves having the frequencies and/or wavelengths identified above reflecting off the terahertz reflective material.

In some embodiments, the saturated hygroscopic material includes hydrous calcium chloride, hydrous calcium sulfate, hydrous potassium carbonate, hydrous sodium sulfate, hydrous cobalt (II) chloride, hydrous lithium chloride, hydrous zinc chloride, hydrous magnesium sulfate, hydrous copper sulfate, hydrous sodium tetraborate, hydrous sodium acetate, hydrous aluminum sulfate, hydrous aluminum potassium sulfate, hydrous magnesium chloride, hydrous sodium potassium tartrate, hydrous sodium thiosulfate, hydrous sodium silicate, hydrous sodium metasilicate, saturated silica gel, saturated microporous clays, saturated zeolites, saturated activated alumina, saturated activated carbon, or a combination thereof.

In some embodiments, the terahertz reflective material includes a metallic film. In some embodiments, the metallic film includes the metals discussed above. In some embodiments, the terahertz reflective material is configured to be retro-reflective.

In some embodiments, the terahertz reflective material includes retro-reflective wells 108. In some embodiments, the saturated hygroscopic material is deposited in one or more of the retro-reflective wells. In some embodiments, each of the retro-reflective wells may have a width as identified above. In some embodiments, the terahertz reflective material is configured to reflect the incident signal.

In some embodiments, the tag identification system further includes a polymer substrate on which the terahertz reflective material is disposed. In some embodiments, the polymer substrate includes the polymers disclosed above. In some embodiments, the saturated hygroscopic material is configured to absorb the incident signal.

In some embodiments, the tag identification system further includes a polymer overlay disposed on the saturated hygroscopic material to seal the saturated hygroscopic material on the terahertz reflective material. In some embodiments, the polymer overlay is transmissive to the incident signal and to the reply signal. In some embodiments, the polymer overlay is water impermeable. In some embodiments, the polymer overlay includes polyethylene terephthalate, polyethylene, high-density polyethylene, acrylic polymer, or a combination thereof.

In some embodiments, the reply signal includes a reflectance pattern formed from absorbance of the incident signal by the saturated hygroscopic material and reflection of the incident signal by the terahertz reflective material. In some embodiments, the tag identification device is further configured to translate the reflectance pattern into readable data. In some embodiments, the tag identification device is a divergent terahertz source or a scanning laser system. In some embodiments, the tag identification device is handheld. In some embodiments, the tag identification device may include terahertz sensitive cameras and sensors.

Some embodiments are directed to a method of using a tag identification system including the steps of transmitting an incident signal toward a tag, wherein the tag includes a saturated hygroscopic material deposited on a terahertz reflective material, and receiving a reply signal from the tag in response to the incident signal. In some embodiments, the method further includes translating the reply signal into readable data, the reply signal including a reflectance pattern formed from absorbance of the incident signal by the saturated hygroscopic material and reflection of the incident signal by the terahertz reflective material. In some embodiments, the incident signal and reply signal independently comprise electromagnetic waves having the frequencies and/or wavelengths identified above.

Some embodiments are directed to a method of making a tag including providing a terahertz reflective material; providing a saturated hygroscopic material; and positioning the saturated hygroscopic material on the terahertz reflective material. In some embodiments, the method further includes positioning the terahertz reflective material on a polymer substrate by vapor deposition. In some embodiments, the method further includes forming the polymer substrate by thermoplastic molding or thermoplastic printing. In some embodiments, the polymer substrate includes the polymers disclosed above.

In some embodiments, the method of making the tag may further include sealing the saturated hygroscopic material onto the terahertz reflective material using a polymer overlay. In some embodiments, sealing the saturated hygroscopic material includes thermally sealing the saturated hygroscopic material with the polymer overlay. In some embodiments, the polymer overlay includes polyethylene terephthalate, polyethylene, high-density polyethylene, acrylic polymer, or a combination thereof. In some embodiments, the polymer overlay is water impermeable. In some embodiments, the polymer overlay is transmissive to electromagnetic waves having the frequencies and/or wavelengths identified above.

In some embodiments, the saturated hygroscopic material includes the saturated hygroscopic material discussed above. In some embodiments, the terahertz reflective material includes a metallic film. In some embodiments, the metallic film includes the metals discussed above.

In some embodiments, the terahertz reflective material is configured to be retro-reflective. In some embodiments, the terahertz reflective material includes retro-reflective wells. In some embodiments, the saturated hygroscopic material is deposited in one or more of the retro-reflective wells. In some embodiments, each of the retro-reflective wells may have a width as identified above. In some embodiments, the terahertz reflective material is configured to reflect electromagnetic waves having the frequencies and/or wavelengths identified above. In some embodiments, the saturated hygroscopic material is configured to absorb electromagnetic waves having the frequencies and/or wavelengths identified above.

In some embodiments, the method further includes forming a reflectance pattern from absorbance of incident electromagnetic waves by the saturated hygroscopic material and reflection of the incident electromagnetic waves by the terahertz reflective material. In some embodiments, the reflectance pattern is translatable into readable data.

In some embodiments, the polymer substrate may be formed by standard thermoplastic moulding or printing techniques. In some embodiments, the polymer substrate has a surface structure that facilitates retro-reflective behavior (for example, imprinted corner reflector wells) of the terahertz reflective material deposited on its surface. In some embodiments, the textured surface of the polymer substrate may be metallized, for example with aluminum, by vapor deposition forming the retro-reflective wells. In some embodiments, the polymer substrate has a thickness of about 15 microns to about 1 millimeter. In some embodiments, the saturated hygroscopic material is positioned into the retro-reflective wells. In some embodiments, the polymer overlay is overlaid on the saturated hygroscopic material deposited terahertz reflective material and thermally sealed.

Figure 6:
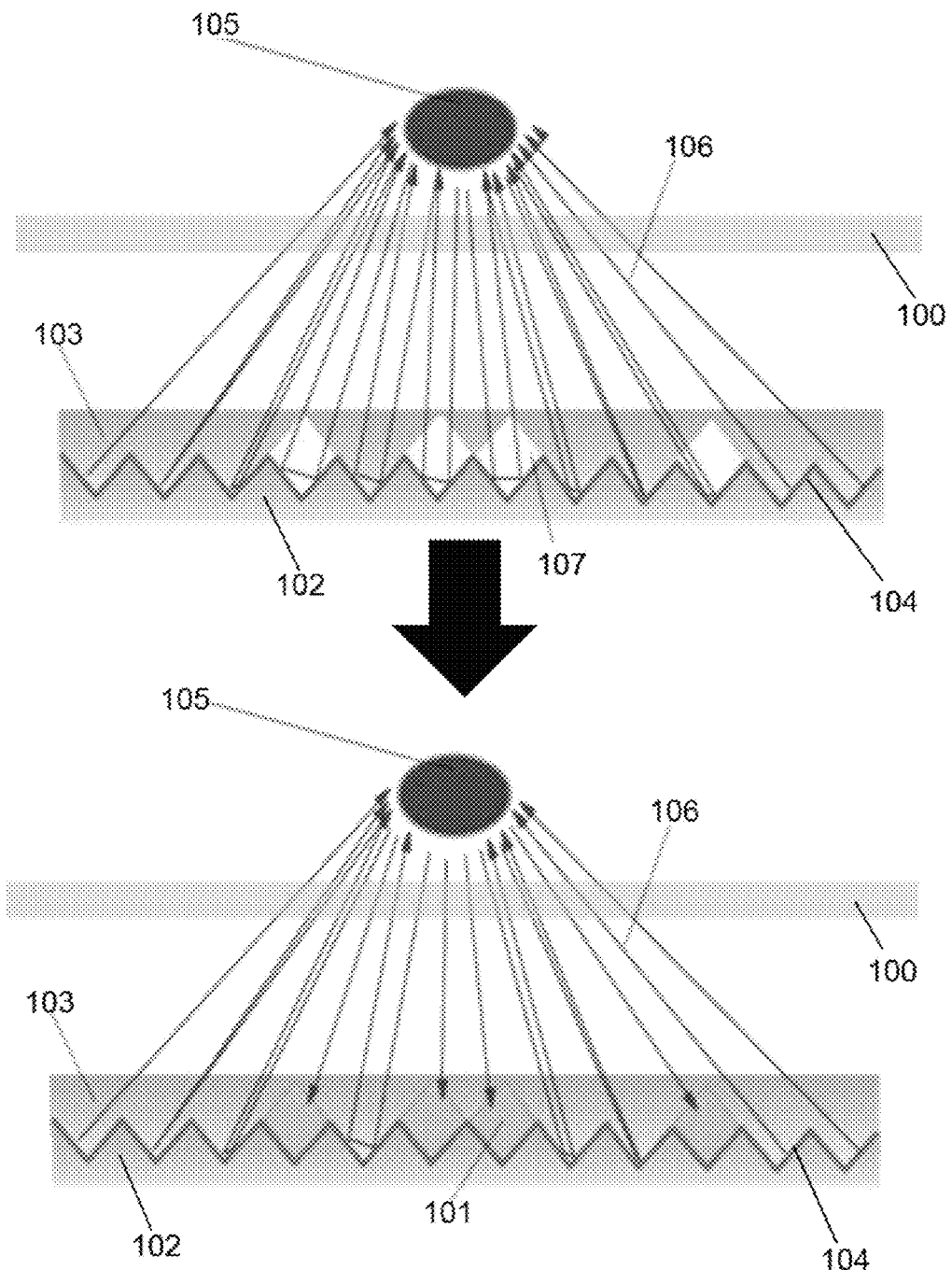
FIG. 6 depicts a cross-sectional view of an illustrative tag having a moisture permeable overlay layered onto an anhydrous salt, which when exposed to a humid atmosphere, absorbs incident terahertz waves according to an embodiment described herein.

Some embodiments herein are directed to a humidity sensor. As shown in FIG. 6, the humidity sensor may include a terahertz reflective material 104; and an anhydrous hygroscopic material 107 positioned on the terahertz reflective material 104. In some embodiments, the humidity sensor further includes a polymer overlay 103 sealing the anhydrous hygroscopic material 101 on the terahertz reflective material 104. In some embodiments, the anhydrous hygroscopic material includes anhydrous calcium chloride, anhydrous calcium sulfate, anhydrous potassium carbonate, anhydrous sodium sulfate, anhydrous cobalt (II) chloride, anhydrous lithium chloride, anhydrous zinc chloride, anhydrous magnesium sulfate, anhydrous copper sulfate, anhydrous sodium tetraborate, anhydrous sodium acetate, anhydrous aluminum sulfate, anhydrous aluminum potassium sulfate, anhydrous magnesium chloride, anhydrous sodium potassium tartrate, anhydrous sodium thiosulfate, anhydrous sodium silicate, anhydrous sodium metasilicate, anhydrous silica gel, anhydrous microporous clays, anhydrous zeolites, anhydrous activated alumina, anhydrous activated carbon, or a combination thereof.

In some embodiments, the polymer overlay includes polyethylene oxide, microporous polyethylene, a polyethylene oxide/polybutylene terephthalate (PEO-PBT) copolymer, sulfonated polyetheretherketone (SPEEK), polydimethylsiloxane, ethyl cellulose, a woven polymer overlay of any of the foregoing, a perforated polymer overlay of any of the foregoing, or a combination thereof. In some embodiments, the polymer overlay is water permeable. In some embodiments, the polymer overlay is transmissive to electromagnetic waves 106 having the frequencies and/or wavelengths identified above.

In some embodiments, as shown in FIG. 6, the anhydrous hygroscopic material 107 forms a saturated hygroscopic material 101 when hydrated. In some embodiments, the anhydrous hygroscopic material 107 is configured to be transparent to electromagnetic waves 106 having the frequencies and/or wavelengths identified above. In some embodiments, the anhydrous hygroscopic material 107 is configured to absorb electromagnetic waves 106 having the frequencies and/or wavelengths identified above when hydrated.

In some embodiments, the terahertz reflective material is configured to reflect electromagnetic waves having the frequencies and/or wavelengths identified above. In some embodiments, the terahertz reflective material includes a metallic film. In some embodiments, the metallic film includes the metals discussed above. In some embodiments, the terahertz reflective material is configured to be retro-reflective. In some embodiments, the terahertz reflective material includes retro-reflective wells. In some embodiments, the anhydrous hygroscopic material is deposited in one or more of the retro-reflective wells. In some embodiments, each of the retro-reflective wells may have a width as identified above.

In some embodiments, the humidity sensor further includes a polymer substrate on which the terahertz reflective material is disposed. In some embodiments, the polymer substrate includes the polymers discussed above.

In some embodiments, at least a portion of the anhydrous hygroscopic material is configured to be hydrated when the sensor is exposed to humidity to form a saturated hygroscopic material, and a reflectance pattern indicative of humidity is formed from absorption of incident electromagnetic waves y the saturated hygroscopic material and reflection of the incident electromagnetic waves by the terahertz reflective material and/or any remaining anhydrous hygroscopic material. In some embodiments, the reflectance pattern indicative of humidity is translatable into readable data indicating humidity level and/or the time of exposure.

Some embodiments are directed to a method of making a humidity sensor including the steps of providing a terahertz reflective material; providing an anhydrous hygroscopic material; and positioning the anhydrous hygroscopic material on the terahertz reflective material. In some embodiments, the method further includes sealing the anhydrous hygroscopic material on the terahertz reflective material using a polymer overlay. In some embodiments, sealing the anhydrous hygroscopic material includes thermally sealing the anhydrous hygroscopic material with the polymer overlay.

In some embodiments, the polymer overlay is transmissive to electromagnetic waves 106 having the frequencies and/or wavelengths identified above. In some embodiments, the method of making a humidity sensor further includes depositing the terahertz reflective material on a polymer substrate by vapor deposition. In some embodiments, the method of making a humidity sensor further includes forming the polymer substrate by thermoplastic molding or thermoplastic printing. In some embodiments, the polymer substrate includes the polymers discussed above.

In some embodiments, the polymer overlay includes polyethylene oxide, microporous polyethylene, a polyethylene oxide/polybutylene terephthalate (PEO-PBT) copolymer, sulfonated polyetheretherketone (SPEEK), polydimethylsiloxane, ethyl cellulose, a woven polymer overlay of any of the foregoing, a perforated polymer overlay of any of the foregoing, or a combination thereof. In some embodiments, the polymer overlay is water permeable.

In some embodiments, the anhydrous hygroscopic material includes anhydrous calcium chloride, anhydrous sodium tetraborate, anhydrous sodium acetate, anhydrous aluminum sulfate, anhydrous aluminum potassium sulfate, anhydrous magnesium chloride, anhydrous sodium potassium tartrate, anhydrous sodium thiosulfate, anhydrous sodium silicate, anhydrous sodium metasilicate, or a combination thereof. In some embodiments, the terahertz reflective material includes a metallic film. In some embodiments, the metallic film includes the metals discussed above.

In some embodiments, the terahertz reflective material is configured to be retro-reflective. In some embodiments, the terahertz reflective material includes retro-reflective wells. In some embodiments, the anhydrous hygroscopic material is deposited in one or more of the retro-reflective wells. In some embodiments, each of the retro-reflective wells may have a width as identified above. In some embodiments, the terahertz reflective material is configured to reflect electromagnetic waves having the frequencies and/or wavelengths identified above. In some embodiments, the anhydrous hygroscopic material is configured to be transparent to electromagnetic waves having the frequencies and/or wavelengths identified above. In some embodiments, the anhydrous hygroscopic material is configured to absorb electromagnetic waves having the frequencies and/or wavelengths identified above when hydrated.

In some embodiments, at least a portion of the anhydrous hygroscopic material is configured to be hydrated when the sensor is exposed to humidity to form a saturated hygroscopic material, and wherein a reflectance pattern indicative of humidity is formed from absorbance of incident electromagnetic waves by the saturated hygroscopic material and reflection of the incident electromagnetic waves by the terahertz reflective material and/or any remaining anhydrous hygroscopic material. In some embodiments, the terahertz waves pass through the anhydrous hygroscopic material, and are reflected by the metallic film. In some embodiments, the anhydrous hygroscopic material is transparent to terahertz waves (allows the passage of terahertz waves). When hydrated, the saturated hygroscopic material absorbs terahertz waves. In some embodiments, the anhydrous hygroscopic material reflects terahertz waves. In some embodiments, the reflectance pattern indicative of humidity is translatable into readable data indicating humidity level and/or the time of exposure.

Some embodiments are directed to a humidity identification system including a humidity sensor having an anhydrous hygroscopic material positioned on a terahertz reflective material. At least a portion of the anhydrous hygroscopic material may be configured to be hydrated when the humidity sensor is exposed to humidity to form a saturated hygroscopic material. The system may further include a humidity sensor identification device configured to transmit an incident signal toward the humidity sensor, and to receive a reply signal from the humidity sensor in response to the incident signal. In some embodiments, the incident signal and the reply signal each independently comprise electromagnetic waves having the frequencies and/or wavelengths identified above.

In some embodiments, the reply signal includes a reflectance pattern indicative of humidity formed from absorption of the incident signal by the saturated hygroscopic material and reflection of the incident signal by the terahertz reflective material and/or any remaining anhydrous hygroscopic material. In some embodiments, the reply signal includes a reflectance pattern indicative of humidity formed from absorption of the incident signal by the saturated hygroscopic material and reflection of the incident signal by the terahertz reflective material. In some embodiments, the reflectance pattern indicative of humidity is translatable into readable data indicating humidity level and/or the time of exposure.

Some embodiments are directed to a method of using a humidity identification system including the steps of transmitting an incident signal toward a humidity sensor, the humidity sensor comprising an anhydrous hygroscopic material positioned on a terahertz reflective material, and at least a portion of the anhydrous hygroscopic material is configured to be hydrated when the humidity sensor is exposed to humidity to form a saturated hygroscopic material. The method may further include receiving a reply signal from the humidity sensor in response to the incident signal.

In some embodiments, the method further includes translating a reflectance pattern formed from absorbance of the incident signal by the saturated hygroscopic material and reflection of the incident signal by the terahertz reflective material and/or any remaining anhydrous hygroscopic material into readable data. In some embodiments, the readable data is indicative of humidity level and/or the time of exposure. In some embodiments, the incident signal and the reply signal each independently comprise electromagnetic waves having the frequencies and/or wavelengths identified above.

Some embodiments relate to a temperature sensor having a terahertz reflective material; an anhydrous hygroscopic material positioned on the terahertz reflective material; and a polymer overlay having thermally controlled water permeability disposed on the anhydrous hygroscopic material to seal the anhydrous hygroscopic material on the terahertz reflective material. In some embodiments, the temperature sensor detects temperature in a humid atmosphere. In some embodiments, any level of humidity would be sufficient for temperature detection by the temperature sensors of embodiments herein.

In some embodiments, a polymer overlay with thermally controlled water permeability may be used to detect whether a tag has been exposed to temperatures above a temperature threshold. In some embodiments, the polymer overlay may comprise polyurethane copolymers for specific point permeability change. In some embodiments, the polymer overlay may comprise acrylic side-chain crystallizable polymers for a slow permeability shift. In some embodiments, the polymer overlay has a critical glass transition temperature as identified above.

In some embodiments, the polymer overlay includes a polyurethane copolymer, an acrylic side-chain crystallizable polymer, siloxane side-chain crystallizable polymer, or a combination thereof. In some embodiments, the polymer overlay has a critical glass transition temperature as identified above. In some embodiments, the thermally controlled water permeability of the polymer overlay is irreversible. In some embodiments, the polymer overlay is transmissive to electromagnetic waves having the frequencies and/or wavelengths identified above.

In some embodiments, the anhydrous hygroscopic material includes anhydrous calcium chloride, anhydrous zinc chloride, anhydrous magnesium sulfate, anhydrous copper sulfate, anhydrous sodium tetraborate, anhydrous sodium acetate, anhydrous aluminum sulfate, anhydrous aluminum potassium sulfate, anhydrous magnesium chloride, anhydrous sodium potassium tartrate, anhydrous sodium thiosulfate, anhydrous sodium silicate, anhydrous sodium metasilicate, or a combination thereof. In some embodiments, the anhydrous hygroscopic material is configured to reflect incident electromagnetic waves having the frequencies and/or wavelengths identified above. In some embodiments, the anhydrous hygroscopic material is configured to be transparent to incident electromagnetic waves having the frequencies and/or wavelengths identified above and allow the terahertz waves to reflect off the terahertz reflective material. In some embodiments, the anhydrous hygroscopic material is configured to absorb electromagnetic waves having the frequencies and/or wavelengths identified above when hydrated.

In some embodiments, the terahertz reflective material is configured to reflect electromagnetic waves having the frequencies and/or wavelengths identified above. In some embodiments, the terahertz reflective material includes a metallic film. In some embodiments, the metallic film includes the metals discussed above.

In some embodiments, the terahertz reflective material is configured to be retro-reflective. In some embodiments, the terahertz reflective material includes retro-reflective wells. In some embodiments, the anhydrous hygroscopic material is deposited in one or more of the retro-reflective wells. In some embodiments, each of the retro-reflective wells may have a width as identified above.

In some embodiments, the temperature sensor further includes a polymer substrate on which the terahertz reflective material is disposed. In some embodiments, the polymer substrate includes the polymers discussed above.

In some embodiments, the polymer overlay is configured to have a water permeability at a temperature to hydrate at least a portion of the anhydrous hygroscopic material to form a saturated hygroscopic material, and a reflectance pattern indicative of exposure of the sensor to the temperature is formed from absorbance of incident electromagnetic waves by the saturated hygroscopic material and reflection of the incident electromagnetic waves by the terahertz reflective material and/or any remaining anhydrous hygroscopic material.

In some embodiments, the reflectance pattern indicative of exposure of the sensor to the temperature is translatable to readable data indicative of the temperature and/or the time of exposure.

Some embodiments are directed to a method of making a temperature sensor including the steps of providing a terahertz reflective material; providing an anhydrous hygroscopic material; positioning the anhydrous hygroscopic material on the terahertz reflective material; and sealing the anhydrous hygroscopic material on the terahertz reflective material with a polymer overlay having thermally controlled water permeability. In some embodiments, the polymer overlay is transmissive to electromagnetic waves having the frequencies and/or wavelengths identified above.

In some embodiments, sealing the anhydrous hygroscopic material includes thermally sealing the anhydrous hygroscopic material with the polymer overlay. In some embodiments, the method further includes depositing the terahertz reflective material on a polymer substrate by vapor deposition. In some embodiments, the method further includes forming the polymer substrate by thermoplastic molding or thermoplastic printing. In some embodiments, the polymer substrate includes the polymers discussed above.

In some embodiments, the anhydrous hygroscopic material includes anhydrous calcium chloride, anhydrous zinc chloride, anhydrous magnesium sulfate, anhydrous copper sulfate, anhydrous sodium tetraborate, anhydrous sodium acetate, anhydrous aluminum sulfate, anhydrous aluminum potassium sulfate, anhydrous magnesium chloride, anhydrous sodium potassium tartrate, anhydrous sodium thiosulfate, anhydrous sodium silicate, anhydrous sodium metasilicate, or a combination thereof.

In some embodiments, the terahertz reflective material includes a metallic film. In some embodiments, the metallic film includes the metals discussed above. In some embodiments, the terahertz reflective material is configured to be retro-reflective. In some embodiments, the terahertz reflective material includes retro-reflective wells.

In some embodiments, the anhydrous hygroscopic material is deposited in one or more of the retro-reflective wells. In some embodiments, each of the retro-reflective wells may have a width as identified above. In some embodiments, the terahertz reflective material is configured to reflect electromagnetic waves having the frequencies and/or wavelengths identified above. In some embodiments, the anhydrous hygroscopic material is configured to reflect electromagnetic waves having the frequencies and/or wavelengths identified above. In some embodiments, the anhydrous hygroscopic material is configured to be transparent to incident electromagnetic waves having the frequencies and/or wavelengths identified above and allow the terahertz waves to reflect off the terahertz reflective material. In some embodiments, the anhydrous hygroscopic material is configured to absorb electromagnetic waves having the frequencies and/or wavelengths identified above when hydrated.

In some embodiments, the polymer overlay includes a polyurethane copolymer, an acrylic side-chain crystallizable polymer, siloxane side-chain crystallizable polymer, or a combination thereof. In some embodiments, the polymer overlay has a critical glass transition temperature as identified above. In some embodiments, the polymer overlay is configured to have a water permeability at a temperature to hydrate at least a portion of the anhydrous hygroscopic material to form a saturated hygroscopic material, and wherein a reflectance pattern indicative of exposure of the sensor to the temperature is formed from absorbance of incident electromagnetic waves by the saturated hygroscopic material and reflection of the incident electromagnetic waves by the terahertz reflective material and/or any remaining anhydrous hygroscopic material.

In some embodiments, the reflectance pattern indicative of exposure of the sensor to the temperature is translatable to readable data indicative of the temperature and/or the time of exposure. Some embodiments are directed to a temperature identification system having a temperature sensor comprising an anhydrous hygroscopic material deposited on a terahertz reflective material, and a polymer overlay having thermally controlled water permeability disposed on the anhydrous hygroscopic material to seal the anhydrous hygroscopic material on the terahertz reflective material, at least a portion of the anhydrous hygroscopic material is configured to be hydrated when the temperature sensor is exposed to a temperature to form a saturated hygroscopic material, and a temperature sensor identification device configured to transmit an incident signal toward the temperature sensor, and to receive a reply signal from the temperature sensor in response to the incident signal.

In some embodiments, the incident signal and the reply signal independently comprise electromagnetic waves having the frequencies and/or wavelengths identified above.

In some embodiments, the polymer overlay has a water permeability when the sensor is exposed to a temperature to hydrate at least a portion of the anhydrous hygroscopic material. In some embodiments, the reply signal includes a reflectance pattern indicative of exposure of the sensor to the temperature formed from absorbance of the incident signal by the saturated hygroscopic material and reflection of the incident signal by the terahertz reflective material and/or any remaining anhydrous hygroscopic material. In some embodiments, the reflectance pattern is translatable into readable data indicative of the temperature and/or the time of exposure.

Some embodiments are directed to a method of using a temperature identification system including the steps of transmitting an incident signal toward a temperature sensor, the temperature sensor comprising an anhydrous hygroscopic material positioned on a terahertz reflective material, and a polymer overlay having thermally controlled water permeability positioned on the anhydrous hygroscopic material to seal the anhydrous hygroscopic material on the terahertz reflective material, at least a portion of the anhydrous hygroscopic material is configured to be hydrated when the temperature sensor is exposed to a temperature to form a saturated hygroscopic material. In some embodiments, the anhydrous hygroscopic material is configured to allow incident electromagnetic waves having the frequencies and/or wavelengths identified above to pass through and reflect off the terahertz reflective material. The method may further include receiving a reply signal from the temperature sensor in response to the incident signal.

In some embodiments, the method further includes translating a reflectance pattern formed from absorbance of the incident signal by the saturated hygroscopic material and reflection of the incident signal by the terahertz reflective material and/or any remaining anhydrous hygroscopic material, into readable data.

In some embodiments, the readable data is indicative of the temperature and/or the time of exposure. In some embodiments, the incident signal and reply signal independently comprise electromagnetic waves having the frequencies and/or wavelengths identified above.

Some embodiments are directed to a tag including a terahertz reflective material; a hygroscopic material positioned on the terahertz reflective material; and a polymer overlay positioned on the hygroscopic material to seal the hygroscopic material on the terahertz reflective material.

In some embodiments, the hygroscopic material includes calcium chloride, zinc chloride, magnesium sulfate, copper sulfate, sodium tetraborate, sodium acetate, aluminum sulfate, aluminum potassium sulfate, magnesium chloride, sodium potassium tartrate, sodium thiosulfate, sodium silicate, sodium metasilicate, or a combination thereof. In some embodiments, the hygroscopic material is hydrous or anhydrous.

In some embodiments, the terahertz reflective material reflects terahertz electromagnetic waves. In some embodiments, the terahertz reflective material includes a metallic film. In some embodiments, the metallic film includes the metals discussed above.

In some embodiments, the terahertz reflective material is configured to be retro-reflective. In some embodiments, the terahertz reflective material includes retro-reflective wells. In some embodiments, the hygroscopic material is deposited in one or more of the retro-reflective wells. In some embodiments, each of the retro-reflective wells may have a width as identified above. In some embodiments, the terahertz reflective material is configured to reflect incident electromagnetic waves having the frequencies and/or wavelengths identified above. In some embodiments, the hygroscopic material is hydrous and is configured to absorb incident electromagnetic waves having the frequencies and/or wavelengths identified above. In some embodiments, the hygroscopic material is anhydrous and is configured to be transparent electromagnetic waves having the frequencies and/or wavelengths identified above.

In some embodiments, the polymer overlay is water permeable. In some embodiments, the polymer overlay includes polyethylene oxide, microporous polyethylene, a polyethylene oxide/polybutylene terephthalate (PEO-PBT) copolymer, sulfonated polyetheretherketone (SPEEK), polydimethylsiloxane, ethyl cellulose, a woven polymer overlay of any of the foregoing, a perforated polymer overlay of any of the foregoing, or a combination thereof.

In some embodiments, the polymer overlay is water impermeable. In some embodiments, the polymer overlay includes polyethylene terephthalate, polyethylene, high-density polyethylene, acrylic polymer, or a combination thereof.

In some embodiments, a water permeability of the polymer overlay is thermally controlled. In some embodiments, the polymer overlay includes a polyurethane copolymer, an acrylic side-chain crystallizable polymer, siloxane side-chain crystallizable polymer or a combination thereof. In some embodiments, the polymer overlay has a critical glass transition temperature as identified above.

In some embodiments, the tag further includes a polymer substrate on which the terahertz reflective material is disposed. In some embodiments, the polymer substrate includes the polymers discussed above.

In some embodiments, a reflectance pattern is formed from absorbance of incident electromagnetic waves by the hygroscopic material in hydrous form, and reflection of the incident electromagnetic waves by the terahertz reflective material and/or the hygroscopic material in anhydrous form.

Tags and sensors of embodiments described herein may be used for inclusion in freight applications, inclusion in products that are sensitive to environmental factors, sterile packaging verification, security applications, internal identification of parts, identification of components, and the like. Exemplary benefits of such sensors and tags include being readable from a single handheld instrument, high contrast reflection over a wide detection angle, long distance interrogation (at least up to 15-20 meters), non-invasive interrogation, a wide range of penetrable materials and compatible contents, no need for detection of RF transmission originating from the tag, no internal processing and simple sensors.

Tags of some embodiments disclosed herein may be used by creating a deliberate and recognizable contrast that increases the robustness of the ability for sensors to detect a coded surface.

EXAMPLES

Example 1: A Tag Having Hydrous Calcium Chloride and a Gold Film

A tag has hydrous calcium chloride positioned on a gold film in a 2D matrix reflectance pattern encoding a unique identifier. The hydrous calcium chloride is sealed onto the gold film by a polymer overlay of polyethylene terephthalate. The side of the gold film, opposite to the side interfacing with the polyethylene terephthalate overlay and hydrous calcium chloride, is bonded to a polycarbonate substrate. The 2D matrix reflectance pattern formed by absorbance of terahertz waves by the hydrous calcium chloride on the gold film, and reflectance of terahertz waves by portions of the gold film not occupied by the hydrous calcium chloride, may be read by a camera style divergent beam interrogator to identify the tagged product.

The camera style divergent beam interrogator sends terahertz waves toward the gold film, where the waves either reflect off the gold film or are absorbed by the hydrous calcium chloride blocking access to the gold film, creating a reflectance pattern which is reflected back to the interrogator and subsequently decoded to identify the tagged product.

Example 2: A Humidity Sensor Having Anhydrous Magnesium Sulfate and a Silver Film A humidity sensor has anhydrous magnesium sulfate positioned on a silver film. The anhydrous magnesium sulfate is sealed onto the silver film by a polymer overlay of polydimethylsiloxane. The polymer overlay is water permeable. The side of the silver film, opposite to the side interfacing with the polydimethylsiloxane overlay and anhydrous magnesium sulfate, is bonded to a polyethylene terephthalate substrate. When not exposed to a humid atmosphere, the anhydrous magnesium sulfate is transparent to terahertz waves (that is it allows terahertz waves to pass through) and the silver film reflects back terahertz waves when interrogated. When exposed to a humid atmosphere, the anhydrous magnesium sulfate is saturated with moisture that permeates through the polymer overlay, to form hydrous magnesium sulphate (heptahydrate). The hydrous magnesium sulphate (heptahydrate), when interrogated by terahertz radiation, absorbs terahertz waves.

A scanning laser system interrogates the humidity sensor by sending terahertz waves toward the sensor, where the terahertz waves either reflect off the silver film or are absorbed by the hydrous magnesium sulfate, creating a reflectance pattern which is reflected back to the interrogator and subsequently decoded to determine if humidity is present. Where the terahertz waves fully reflect back from the silver film and the reflectance pattern shows no regions of terahertz wave absorption (for example, regions that appear dark on the reflectance pattern), the sensor indicates that no humidity is present. In contrast, where the reflectance pattern contains regions of terahertz wave absorption, the sensor indicates presence of humidity.

Example 3: A Temperature Sensor Having Anhydrous Zinc Chloride and an Aluminum Film A temperature sensor has anhydrous zinc chloride positioned on an aluminum film. The anhydrous zinc chloride is sealed onto the aluminum film by a polymer overlay of polyurethane copolymer, which is water permeable at 24° C., being the glass transition temperature of the copolymer. The side of the aluminum film, opposite to the side interfacing with the polyurethane copolymer overlay and anhydrous zinc chloride, is bonded to a polyvinylchloride substrate. When not exposed to a temperature above 24 degrees, the anhydrous zinc chloride is transparent to terahertz waves (that is it allows terahertz waves to pass through) and the aluminum film reflects back terahertz waves when interrogated. When exposed to a temperature above 24 degrees, the anhydrous zinc chloride is saturated forming hydrous zinc chloride which when interrogated by terahertz radiation, absorbs terahertz waves.

A scanning laser system interrogates the temperature sensor by sending terahertz waves toward the sensor, where the terahertz waves either reflect off the aluminum film or are absorbed by the water particles in the hydrous zinc chloride, creating a reflectance pattern which is reflected back to the interrogator and subsequently decoded to determine if a temperature threshold has been exceeded. Where the terahertz waves fully reflect back from the aluminum film and the reflectance pattern shows no regions of terahertz wave absorption (for example, regions that appear dark on the reflectance pattern), the sensor indicates that the temperature threshold has not been exceeded. In contrast, where the reflectance pattern contains regions of terahertz wave absorption, the sensor indicates that the temperature threshold has been exceeded.

The present disclosure is not to be limited in terms of the particular embodiments described in this application, which are intended as illustrations of various aspects. Many modifications and variations can be made without departing from its spirit and scope, as will be apparent to those skilled in the art. Functionally, equivalent methods and apparatuses within the scope of the disclosure, in addition to those enumerated in this document, will be apparent to those skilled in the art from the foregoing descriptions. Such modifications and variations are intended to fall within the scope of the appended claims. The present disclosure includes the full scope of equivalents to which the claims are entitled. It is to be understood that this disclosure is not limited to particular methods, reagents, compounds, compositions or biological systems, which can, of course, vary. It is also to be understood that the terminology used in this document is for the purpose of describing particular embodiments only, and is not intended to be limiting.

With respect to the use of substantially any plural and/or singular terms in this document, those having skill in the art can translate from the plural to the singular and/or from the singular to the plural as is appropriate to the context and/or application. The various singular/plural permutations may be expressly set forth in this document for sake of clarity.

It will be understood by those within the art that, in general, terms used in this document, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed in this document also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed in this document can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 bonds refers to groups having 1, 2, or 3 bonds. Similarly, a group having 1-5 bonds refers to groups having 1, 2, 3, 4, or 5 bonds, and so forth.

From the foregoing, it will be appreciated that various embodiments of the present disclosure have been described in this document for purposes of illustration, and that various modifications may be made without departing from the scope and spirit of the present disclosure. Accordingly, the various embodiments disclosed in this document are not intended to be limiting, with the true scope and spirit being indicated by the following claims.

What is claimed is:

1. A tag comprising:
   a terahertz reflective material; and
   a saturated hygroscopic material positioned on the terahertz reflective material, wherein:
   the terahertz reflective material is configured to reflect incident electromagnetic waves, the saturated hygroscopic material is configured to absorb the incident electromagnetic waves, and
   a reflectance pattern is formed from the absorption of the incident electromagnetic waves by the saturated hygroscopic material and the reflection of the incident electromagnetic waves by the terahertz reflective material.

2. The tag of claim 1, wherein the saturated hygroscopic material comprises hydrous calcium chloride, hydrous calcium sulfate, hydrous potassium carbonate, hydrous sodium sulfate, hydrous cobalt (II) chloride, hydrous lithium chloride, hydrous zinc chloride, hydrous magnesium sulfate, hydrous copper sulfate, hydrous sodium tetraborate, hydrous sodium acetate, hydrous aluminum sulfate, hydrous aluminum potassium sulfate, hydrous magnesium chloride, hydrous sodium potassium tartrate, hydrous sodium thiosulfate, hydrous sodium silicate, hydrous sodium metasilicate, saturated silica gel, saturated microporous clays, saturated zeolites, saturated activated alumina, saturated activated carbon, or a combination thereof.

3. The tag of claim 1, wherein the terahertz reflective material comprises a metallic film.

4. The tag of claim 3, wherein the metallic film comprises aluminum, gold, silver, copper, tin, silicon, zinc, nickel, chromium, an alloy of any of the foregoing, or a combination thereof.

5. The tag of claim 1, wherein the terahertz reflective material is configured to be retro-reflective.

6. The tag of claim 1, wherein the terahertz reflective material comprises retro-reflective wells, and wherein the saturated hygroscopic material is positioned in one or more of the retro-reflective wells.

7. The tag of claim 1, wherein the terahertz reflective material is configured to reflect the incident electromagnetic waves at frequencies of about 0.3 terahertz to about 3 terahertz.

8. The tag of claim 1, further comprising a polymer substrate on which the terahertz reflective material is disposed.

9. The tag of claim 1, wherein the saturated hygroscopic material is configured to absorb the incident electromagnetic waves at frequencies of about 0.3 terahertz to about 3 terahertz.

10. The tag of claim 1, wherein the reflectance pattern is translatable into readable data.

11. A tag identification system comprising:
a tag comprising a saturated hygroscopic material positioned on a terahertz reflective material; and
a tag identification device configured to transmit an incident signal towards the tag, and to receive a reply signal from the tag in response to the transmission of the incident signal,
wherein:
the saturated hygroscopic material is configured to absorb the incident signal,
the terahertz reflective material is configured to reflect the incident signal, and
the reply signal comprises a reflectance pattern formed from the absorbance of the incident signal by the saturated hygroscopic material and the reflection of the incident signal by the terahertz reflective material.

12. The tag identification system of claim 11, wherein the incident signal comprises electromagnetic waves at frequencies of about 0.3 terahertz to about 3 terahertz.

13. The tag identification system of claim 11, wherein the reply signal comprises electromagnetic waves at frequencies of about 0.3 terahertz to about 3 terahertz reflecting off the terahertz reflective material.

14. The tag identification system of claim 11, wherein the saturated hygroscopic material comprises hydrous calcium chloride, hydrous calcium sulfate, hydrous potassium carbonate, hydrous sodium sulfate, hydrous cobalt (II) chloride, hydrous lithium chloride, hydrous zinc chloride, hydrous magnesium sulfate, hydrous copper sulfate, hydrous sodium tetraborate, hydrous sodium acetate, hydrous aluminum sulfate, hydrous aluminum potassium sulfate, hydrous magnesium chloride, hydrous sodium potassium tartrate, hydrous sodium thiosulfate, hydrous sodium silicate, hydrous sodium metasilicate, saturated silica gel, saturated microporous clays, saturated zeolites, saturated activated alumina, saturated activated carbon, or a combination thereof.

15. The tag identification system of claim 11, wherein the terahertz reflective material comprises a metallic film.

16. The tag identification system of claim 15, wherein the metallic film comprises aluminum, gold, silver, copper, tin, silicon, zinc, nickel, chromium, an alloy of any of the foregoing, or a combination thereof.

17. The tag identification system of claim 11, wherein the terahertz reflective material is configured to be retro-reflective.

18. The tag identification system of claim 11, wherein the terahertz reflective material comprises retro-reflective wells, wherein the saturated hygroscopic material is deposited in one or more of the retro-reflective wells.

19. The tag identification system of claim 11, further comprising a polymer overlay disposed on the saturated hygroscopic material to seal the saturated hygroscopic material on the terahertz reflective material.

20. The tag identification system of claim 19, wherein the polymer overlay is transmissive to the incident signal and to the reply signal.

21. The tag identification system of claim 19, wherein the polymer overlay comprises polyethylene terephthalate, polyethylene, high-density polyethylene, acrylic polymer, or a combination thereof.

22. The tag identification system of claim 11, wherein the tag identification device is further configured to translate the reflectance pattern into readable data.

23. A method to use a tag identification system, the method comprising:
transmitting an incident signal towards a tag, wherein the tag comprises a saturated hygroscopic material deposited on a terahertz reflective material; and
receiving a reply signal from the tag in response to the transmission of the incident signal, wherein the saturated hygroscopic material is configured to absorb the incident signal, wherein the terahertz reflective material is configured to reflect the incident signal, and wherein the reply signal comprises a reflectance pattern formed from the absorbance of the incident signal by the saturated hygroscopic material and the reflection of the incident signal by the terahertz reflective material.

24. The method of claim 23, further comprising translating the reply signal into readable data.

25. The method of claim 23, wherein transmitting the incident signal comprises transmitting an incident signal comprising electromagnetic waves at frequencies of about 0.3 terahertz to about 3 terahertz, and wherein receiving the reply signal comprises receiving a reply signal comprising electromagnetic waves at frequencies of about 0.3 terahertz to about 3 terahertz.

* * * * *